US007763766B2

(12) United States Patent
Bozzano et al.

(10) Patent No.: US 7,763,766 B2
(45) Date of Patent: Jul. 27, 2010

(54) METHANOL-TO-OLEFINS PROCESS WITH REDUCED COKING

(75) Inventors: Andrea G. Bozzano, Northbrook, IL (US); Steven A. Bradley, Arlington Heights, IL (US); Ricardo L. Castillo, Arlington Heights, IL (US); John Q. Chen, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 470 days.

(21) Appl. No.: 11/315,933

(22) Filed: Dec. 22, 2005

(65) Prior Publication Data
US 2007/0203383 A1    Aug. 30, 2007

(51) Int. Cl.
*C07C 1/00* (2006.01)
*C10G 75/04* (2006.01)
*C10G 9/16* (2006.01)

(52) U.S. Cl. .................. 585/640; 585/639; 208/48 AA; 208/48 R

(58) Field of Classification Search ......... 585/638–640, 585/950; 208/48 R, 48 AA
See application file for complete search history.

(56) References Cited

U.S. PATENT DOCUMENTS

| 4,046,190 | A |   | 9/1977  | Marcus et al. .............. 165/105 |
| 4,328,384 | A |   | 5/1982  | Daviduk et al. ............ 585/469 |
| 4,547,616 | A |   | 10/1985 | Avidan et al. ............... 585/640 |
| 4,677,243 | A |   | 6/1987  | Kaiser ........................ 585/638 |
| 4,692,234 | A | * | 9/1987  | Porter et al. ............ 208/48 AA |
| 4,973,792 | A |   | 11/1990 | Lewis et al. ................. 585/638 |
| 5,406,014 | A |   | 4/1995  | Heyse et al. ................. 585/444 |
| 5,873,951 | A | * | 2/1999  | Wynns et al. ............... 148/242 |
| 6,166,282 | A |   | 12/2000 | Miller ........................ 585/638 |
| 6,482,311 | B1 | * | 11/2002 | Wickham et al. ....... 208/48 AA |
| 6,548,030 | B2 |   | 4/2003  | Heyse et al. ................ 422/240 |
| 6,602,483 | B2 |   | 8/2003  | Heyse et al. ............. 423/418.2 |
| 2004/0102668 | A1 |   | 5/2004 | Lumgair et al. ............ 585/638 |
| 2004/0152935 | A1 |   | 8/2004 | Jones et al. ................. 585/530 |
| 2004/0224839 | A1 |   | 11/2004 | Wang et al. ................. 502/214 |

FOREIGN PATENT DOCUMENTS

| EP | 0134555 A1 | | 3/1985 |
| WO | WO 2005/005348 | * | 1/2005 |
| WO | WO 2005/005348 A1 | | 1/2005 |

OTHER PUBLICATIONS

"Conversion of Methanol to Gasoline Extended Project: Methanol to Olefins/Modification and Operations of the Demonstration Plant/ Milestone Report" Department of Energy Report DOE/ET/14914 Apr. 1986.
"Effect of Oxidizing and Reducing Gas Atmospheres on the Iron-Catalyzed Formation of Filamentous Carbon from Methanol" IND. ENG.CHEM.RES. 1994, 33, 1367-1372.

* cited by examiner

*Primary Examiner*—In Suk Bullock
(74) *Attorney, Agent, or Firm*—Mark Goldberg

(57) ABSTRACT

A process for producing light olefins from oxygenates wherein internal reactor are protected from metal-catalyzed coking preferably by employing a protective layer.

14 Claims, 4 Drawing Sheets

METHANOL-TO-OLEFINS PROCESS WITH REDUCED COKING

FIELD OF THE INVENTION

The present invention relates generally to hydrocarbon conversion processes utilizing a fluidized bed reaction zone. More particularly, the present invention relates to a process and a reactor section for use in the conversion of methanol to light olefins.

BACKGROUND OF THE INVENTION

Light olefins, particularly ethylene and propylene, are important intermediates in the manufacture of a variety of chemical products. The limited availability and high cost of petroleum sources has caused an increase in the cost of producing light olefins from such sources. Together with geographic differences in availability and rapid petrochemical growth in developing economies, these factors are promoting a search for alternative materials for light-olefin production. Oxygenates such as alcohols, more particularly methanol and ethanol, may be produced by fermentation or from synthesis gas. Synthesis gas can be produced from natural gas, petroleum liquids, and carbonaceous materials including coal, recycled plastics, municipal wastes, or other organic materials. Thus, alcohols provide alternative routes for the production of olefins and derivatives.

The conversion of methanol to yield light olefins is well known. "Hydrocarbons from Methanol" by Clarence D. Chang, published by Marcel Dekker, Inc. N.Y. (1983) presents a survey and summary of the technology described by its title. Chang discussed methanol-to-olefin conversion in the presence of molecular sieves at pages 21-26. The examples given by Chang as suitable molecular sieves for converting methanol to olefins are chabazite, erionite, and synthetic zeolite ZK-5.

U.S. Pat. No. 4,328,384 and U.S. Pat. No. 4,547,616 teach conversion of oxygenates to olefins using a fluidized zeolite catalyst. The use of a silicoaluminophosphate molecular sieve to produce light olefins from aliphatic hetero compounds is disclosed in U.S. Pat. No. 4,677,243. U.S. Pat. No. 4,973,792 teaches fluidized catalytic conversion of hetero compounds to light olefins including a purge prior to regeneration of the catalyst. U.S. Pat. No. 6,166,282 teaches oxygenate conversion using a fast-fluidized-bed reactor featuring reduced catalyst inventory compared to earlier processes. The teachings of all of the above patents are incorporated herein by reference thereto.

The art discloses coating of processing equipment in several instances to prevent undesirable side reactions. U.S. Pat. No. 6,548,030 inter alia teaches a low-sulfur catalytic reforming system with at least one surface portion having a protective layer to resist carburization and metal dusting. U.S. Pat. No. 5,406,014 discloses a method for dehydrogenation in which a steel reactor system is provided with a protective layer to resist carburization. U.S. Pat. No. 6,602,483 B2 teaches a hydrocarbon conversion process using steam, exemplified by thermal cracking and ethylbenzene dehydrogenation, in which the steam requirement is reduced by a metal-containing coating on the reactor system. US 2004/0152935 A1 discloses a method for reducing metal-catalyzed byproducts from undesirable methanol conversion in a feed vaporization and introduction system up to the point that methanol enters a methanol-to-olefins reactor by coating heaters, feed lines and feed nozzles. William L Holstein teaches that the presence of water in chemical processes involving methanol maintains iron surfaces in an oxide state which is inactive for the formation of filamentous carbon in IND. ENG. CHEM. RES. 1994, 33, 1363-1372.

The Department of Energy report DOE/ET/14914 of April, 1986, CONVERSION OF METHANOL TO GASOLINE Extended Project: METHANOL TO OLEFINS/Modification and Operations of the Demonstration Plant/MILESTONE REPORT covers a methanol-to-olefins demonstration project using a modified 100 barrel-per-day plant which previously had been used for demonstration of a methanol-to-gasoline [MTG] project. Experimental runs in the demonstration plant showed that at 375° C. carbon steel can catalyze methanol decomposition, necessitating replacement of the superheater with a new one made from stainless steel. U.S. Pat. No. 4,046,190 is drawn to a heat pipe device comprising capillary grooves and metal wicking between the plates, and discloses that "It has been found that copper, brass, nickel and stainless steel are compatible with methanol at 55° F." The publication, "Effect of Oxidizing and Reducing Gas Atmospheres on the Iron-Catalyzed Formation of Filamentous Carbon from Methanol, IND. ENG. CHEM. RES. 1994, 33, 1367-1372, discusses methanol decomposition and filamentous carbon formation on iron surfaces, recognizing longer induction periods for stainless steel.

The above references acknowledge the issue of metal-catalyzed coking when converting an oxygenate in a fluidized-bed reaction zone, but suggest that the problem may be avoided by the use of water in the process or with stainless-steel equipment. The present invention identifies the unanticipated problem of metal-catalyzed coking under these conditions and offers a solution for protection of the surfaces of a reaction zone.

SUMMARY OF THE INVENTION

In a broad embodiment, the invention comprises a process to convert a feed stream comprising an oxygenate in a fluidized-bed reaction zone at conversion conditions in the presence of a catalyst to yield a product stream comprising light olefins, wherein one or more of the internal surfaces of the reaction zone has a resistance to metal-catalyzed coking greater than that of alloy steel.

A more specific embodiment is a process to convert a feed stream comprising an oxygenate in a fluidized-bed reaction zone at conversion conditions in the presence of a catalyst to yield a product stream comprising light olefins, wherein one or more of the internal surfaces of the reaction zone comprises a protective layer resistant to metal-catalyzed coking.

A yet more specific embodiment is a process to convert a feed stream comprising an oxygenate in the reaction zone of a fast-fluidized-bed reactor at conversion conditions in the presence of a catalyst to yield a product stream comprising light olefins, wherein the one or more of the internal surfaces of the reaction zone comprises a protective layer resistant to metal-catalyzed coking.

In an alternative embodiment, the invention is process to convert a feed stream comprising an oxygenate in a fluidized-bed reaction zone at conversion conditions in the presence of a catalyst to yield a product stream comprising light olefins, further comprising introducing an organometallic compound in the feed stream to reduce metal-catalyzed coking.

These and other objects and embodiments will become evident from the following detailed description of the invention.

DETAILED DESCRIPTION OF THE INVENTION

Aliphatic hetero compounds are particularly preferred feed streams for use in the present invention, especially when light olefins, i.e., olefins containing 2 to about 6 and preferably 2 to 4 carbon atoms per molecule are to be produced. The term "aliphatic hetero compounds" is employed herein to include alcohols, halides, mercaptans, sulfides, amines, ethers and carbonyl compounds, e.g., aldehydes, ketones, carboxylic acids and the like. The aliphatic moiety preferably contains from 1 to about 10 carbon atoms, and more preferably from about 1 to 4 carbon atoms. Examples of suitable aliphatic hetero compounds include: methanol, methyl mercaptan, methyl sulfide, methyl amine, dimethyl ether, ethanol, ethyl mercaptan, ethyl chloride, diethyl ether, methylethyl ether, formaldehyde, dimethyl ketone, acetic acid, alkyl amines, alkyl halides, and alkyl sulfides. In the aspect of the invention where light olefins and/or gasoline range hydrocarbons are the desired products, the feed stream is preferably selected from methanol, ethanol, dimethyl ether, diethyl ether, and mixtures thereof, with methanol being particularly preferred.

The product or products obtained from the conversion process will depend inter alia on the feed stream, catalyst and conditions employed. The desired product usually is organic, preferably hydrocarbons in the $C_2$ to $C_6$ carbon range. An especially preferred product comprises light olefins having from about 2 to 6, more preferably from about 2 to 4, carbon atoms per molecule. The desired product or products preferably have kinetic diameters which allow such product or products to be removed from or escape from the pores of a catalyst employed in the conversion process. An optimal product comprises one or both of ethylene and propylene.

The invention is advantageously applied to any fluidized-bed reaction zone for converting oxygenates to light olefins. For example, the features of the invention can be used in a bubbling-bed reactor system as described in the known art. The bubbling bed reactor comprises a lower reaction zone to contain the actual bubbling bed of fluidized catalyst and a disengaging zone which contains, typically, a three-stage cyclone separation system to remove catalyst particles from the products of the reaction. Conventional catalyst coolers are employed within the bubbling bed to remove heat from the exothermic reaction.

Preferably, the process employs a fast-fluidized-bed reactor as disclosed in U.S. Pat. No. 6,166,282, incorporated herein by reference as noted previously. The reaction zone comprises a dense-phase zone, a disengaging zone comprising at least a portion of a transition-phase zone, a separation zone, and two-stages of cyclone separation. This system is described below for illustrative purposes and is not intended to limit the scope of the claims that follow.

Figure 1:
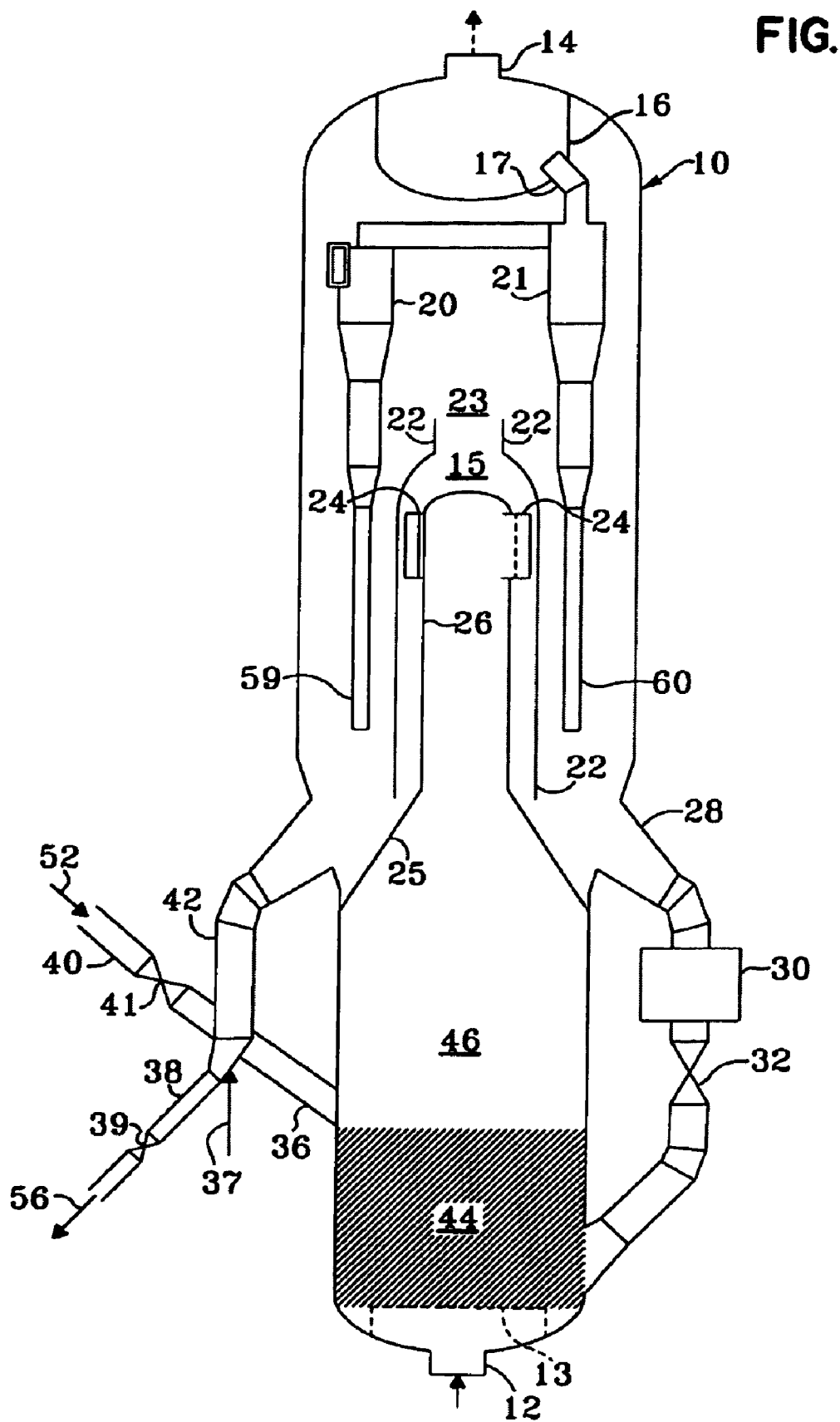
FIG. 1 is a schematic diagram of a fast-fluidized-bed reactor embodiment to aid in understanding the present invention.

Referring to FIG. 1, a fast-fluidized-bed reactor 10 for the production of light olefins from oxygenates is illustrated in schematic form. The fast-fluidized-bed reactor comprises a disengaging zone 15 and a lower reaction zone consisting of a dense-phase zone 44 and a transition-phase zone 46. A feed stream enters the reactor via feed inlet 12 in the presence of a diluent. The feedstock and diluent admixture passes through a feed distributor 13 and enters the dense-phase zone 44. The feed distributor 13 consists of a uniformly flat or curved sieve plate which permits the vapor phase feed admixture to pass through while retaining a catalyst above the sieve plate. Generally, the feed distributor 13 is supported by a ring attached to a plurality of legs disposed on the base of the reactor to support the ring.

The feedstock contacts a catalyst in dense-phase zone 44 and reacts at effective conditions to yield a product stream comprising light olefins. The product stream and catalyst mixture comprising active catalyst and some catalyst which has become deactivated are conveyed into the transition-phase zone 46 and continue moving upwardly through the lower reaction zone into a riser section 26. The cross-sectional area of the flow path through the fast-fluidized-bed reactor is reduced from the cross-sectional area of the dense-phase zone by a reducing means 25, or cone section, to the cross-sectional area of the riser section. The fast-fluidized-bed reaction zone provides more precise control of the feedstock and catalyst rates and provides significantly decreased catalyst inventories over a bubbling bed reactor.

The riser section 26 discharges the reaction product stream and catalyst mixture through a separation zone to a discharge opening, comprising distributor arms 24, and a separation vessel 22. The discharge opening 24 tangentially discharges the product stream and catalyst mixture to provide an initial stage cyclonic separation. The catalyst mixture falls to the bottom of the disengaging zone 15 through a particle outlet for discharging fluidized catalyst particles, and the product stream passes upwardly through a gas recovery outlet 23 for withdrawing gaseous fluids from the separation vessel 22. The product stream and entrained catalyst continue to a dilute-phase separator typically in the form of a series of one to three conventional cyclone separation stages shown in the drawing as 20 and 21. Primary separation stage 20 passes a vapor stream to a secondary cyclone separation stage 21, and the vapor from the secondary cyclone separation stage 21 is conveyed via conduit 17 to a plenum chamber 16. A net product stream is withdrawn from the reactor outlet 14.

Catalyst separated in the cyclone separation stages 20 and 21 drops respectively through dipleg 59 and 60 into the bottom of the disengaging zone 15. Diplegs 59 and 60 are fitted with flapper valves (not shown) at their base to prevent the back flow of vapors through the cyclone separators. Catalyst accumulates in the bottom of the disengaging zone 15. and any excess catalyst is passed through at least one external catalyst recirculation standpipe 28 through a recirculation slide valve 32 to the dense-phase zone 44. Optionally, a heat transfer zone 30, such as a conventional flow-through catalyst cooler, is disposed in at least one external catalyst recirculation standpipe at a point above the recirculation slide valve 32.

To maintain the conversion and selectivity of the reaction at acceptable levels, a portion of the catalyst mixture is withdrawn as a spent catalyst stream from the upper disengaging zone 15 and passed through a spent catalyst standpipe 42. In the spent catalyst standpipe 42, the spent catalyst stream is stripped with a stripping medium such as steam introduced in line 37 to produce a stripped catalyst stream 56. The spent catalyst standpipe 42 will typically include a stripping section that contains grids or baffles to improve contact between the catalyst and the stripping medium. The stripped catalyst stream is conveyed through line 38 and the spent catalyst slide valve 39. The stripped catalyst stream 56 is passed to a catalyst regeneration zone (not shown). In the catalyst regeneration zone, the spent catalyst stream is at least partially regenerated either by oxidation or reduction to produce a regenerated catalyst stream by means well known to those skilled in the art of fluidized-bed reaction systems. A regenerated catalyst stream 52 is returned to the lower reaction zone via a regenerated catalyst standpipe comprising line 40, regenerated catalyst slide valve 41, and line 36 to a point above the dense-phase zone 44.

The "reaction zone" of the present invention comprises equipment of the present process which is exposed to the feed stream, product stream, catalyst and intermediate reactants and products at elevated temperatures that may effect metal-catalyzed coking under circumstances of the known art. Internal surfaces of such equipment which should have a resistance to metal-catalyzed coking greater than that of alloy steel when utilizing the present invention may comprise, without limitation, the inner surface of the reactor, reducing means, riser, separation zone including cyclones, conduit, plenum chamber, diplegs, standpipes and catalyst cooler. In the fast-fluidized-bed embodiment described above, such internal surfaces may comprise, for example without so limiting the invention, the one or more of the internal surfaces of reactor 10 including zones and sections 15, 44, 46, 22, 24, 25 and 26; cyclones 20 and 21 with diplegs 59 and 60; conduit 17, chamber 16; and catalyst-handling equipment 36, 37, 38, 39, 40, 41, 42, 56 and 30. The surfaces may comprise any material which is effective to carry out the fast-fluidized-bed conversion, and usually comprise one or more of steel and refractory materials having antiwear properties with the latter generally being anchored by such materials as Hexmesh, s-bar, wavy V anchors. Optionally the reaction zone comprises part or all of a feed distributor such as section 13, although in this event preferably only the flat or curved sieve plate exposed to reaction temperatures and not feed-introduction nozzles are within the scope of the present invention.

The reaction zone conventionally may have surfaces of alloy steel, such as 1¼-Cr-½-Mo steel, 9-Cr-1-Mo steel or the stainless steels and the like as known in the fluidized-bed reactor art. Stainless steels, such as Types 304, 316, 310, 321 and 347 stainless steels, have a greater resistance than carbon steel to metal-catalyzed coking. When converting oxygenates to light olefins, however, best results are achieved using the teachings of the present invention to provide a protective layer to internal surfaces of the reaction zone.

Metal-catalyzed coking leads to the formation of filamentous carbon, which promotes corrosion of reactor walls and coking of the catalyst (Holstein, op. cit., p. 1363). The carbon fibers may effect obstruction or clogging of moving parts (e.g., valve hinges) and increased pressure drops or even plugging of restricted spaces (e.g., diplegs). Metal-catalyzed coking also may be associated with carburization, although examination of iron surfaces exposed to conditions related to the present invention indicates that filamentous carbon is the principal concern.

Best results thus are achieved when one or more of the internal surfaces of the reaction zone of the present invention comprises a protective layer resistant to metal-catalyzed coking. The protective layer may be formed on the one or more of the internal surfaces of the reaction zone using at least one of a variety of materials applied in any manner which is effective to provide a stable layer at conversion conditions. Effective materials can be selected from one or more of, without so limiting the invention, tin, chromium, antimony, aluminum, germanium, bismuth, arsenic, gallium, indium, lead, copper, molybdenum, tungsten, titanium, niobium, zirconium, tantalum, hafnium, silver, gold, platinum, and mixtures, intermetallic compounds and alloys, as well as silicon and alumina. Preferred metals are selected from one or more of the group consisting of tin, chromium, nickel, antimony, aluminum, germanium and silicon.

The protective layer may be applied in any suitable manner which provides a stable layer at conversion conditions. For example, without so limiting the invention, metal-containing coatings can be applied by painting, electroplating, cladding, spraying, chemical vapor deposition, and sputtering. Painting is a preferred method of applying the protective layer. Such paint can be applied on reactor-system surfaces by any effective manner such as spraying, brushing, or pigging, Preferably, the paint is a decomposable, reactive, metal-containing paint which produces a reactive metal which interacts with the reaction-zone internal surface. Tin is a preferred metal and is exemplified herein; disclosures herein about tin are generally applicable to other reducible metals such as germanium. Preferred paints comprise a metal component selected from one or more of the group comprising: a hydrogen-decomposable metal compound, such as an organometallic compound; finely divided metal; a metal oxide, preferably a reducible metal oxide; and a solvent. A particularly preferred organometallic compound comprises one or more of butyl tin, tin octanoate or tin neodecanoate. It is within the scope of the invention that iron is added to a tin-containing paint to facilitate the reaction of the paint to form iron stannides as a flux.

In a further alternative embodiment, one or both of aluminum and silicon can be applied to metal surfaces such as steels by well known deposition techniques. Alternative processes include powder and vapor diffusion processes such as the "Alonizing" process, which has been commercialized by Alon Processing, Inc., Tarentum, Pa. Essentially, "Alonizing" is a high temperature diffusion process which alloys aluminum into the surface of a treated metal, such as steel, producing aluminides. Silicon can be applied by any effective method; for example, by diffusion coating as disclosed in U.S. Pat. No. 4,714,632; U.S. Pat. No. 5,254,369; and U.S. Pat. No. 5,873,951. As disclosed in these patents, other materials such as aluminum and chromium may be combined with silicon in a protective coating.

It is preferred that the coatings be sufficiently thick that they completely cover the base metallurgy and that the resulting protective layers remain intact over years of operation. This thickness depends, inter alia, on the nature and effectiveness of the coating metal. In general, the thickness after curing is preferably between about 0.1 and 50 mils, more preferably between about 0.5 and 10 mils.

Although not necessary for all coating materials, for some coatings it is preferred that the coating be cured prior to use. This is especially true for coating materials containing reducible metal oxides and organometallic components, such as oxygen-containing organometallic compounds.

In a preferred embodiment, cure conditions comprise a heating step and optionally a reducing step in a hydrogen-containing atmosphere at elevated temperatures. Hydrogen contacting preferably occurs while the protective layer is being formed. In general, the contacting of the reactor system having a metal-containing coating, plating, cladding, paint or other coating applied to a portion thereof with a hydrogen-containing gas is done for a time and at a temperature sufficient to produce a continuous and uninterrupted protective layer which adheres to the substrate. Curing is preferably done over a period of hours, often with temperatures increasing over time. For example, tin paints are preferably cured between 480° and 600° C.

Alternatively or in addition to directly coating the one or more of the internal surfaces, a protective layer to reduce metal-catalyzed coking can be provided by introducing protective materials in the feed stream. Preferably the protective material is introduced as an organometallic compound which optimally is a hydrogen-decomposable compound. Preferable organometallic compounds are selected from compounds of tin, chromium, antimony, aluminum and germanium, with tin compounds being especially favored. Such materials should be mobile and able to bond with the one or more of the internal surfaces. For example, one or more of butyl tin, tin octanoate and tin neodecanoate could be introduced into the feed stream in a concentration of from about 0.01 to 500 wt-ppm. The organometallic compound may be introduced either on a continuous basis or on an intermittent basis in a cycle sufficient to provide a protective layer as described hereinbefore to reduce metal-catalyzed coking.

Suitable reaction conditions for the conversion of aliphatic hetero compounds vary by the nature of the feed stream and product objective. In general, reaction severity increases with increasing temperature, increasing catalyst activity, and decreasing space velocity. Suitable conditions for the conversion of oxygenates to light olefins in accordance with the present invention comprise a temperature of from about 200° to 600° C., preferably from about 300° to 500° C., and a pressure of from about 7 to 1400 kPa, preferably from about 140 to 700 kPa.

A diluent can be added to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons (e.g., methane), aromatic hydrocarbons (e.g., benzene, toluene), and mixtures thereof. The amount of diluent used can vary considerably and is usually from about 5 to about 90 mol-% of the feedstock and preferably from about 25 to about 75 mol-%. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to about 0.1 to 5 moles of water have been disclosed.

The present invention is not limited to specific catalysts. Suitable catalysts comprise microporous crystalline materials, a substantial discussion of which can be found in U.S. Pat. No. 4,677,243 which is incorporated herein by reference. Preferred catalysts for use in the present invention comprise non-zeolitic molecular sieves, especially silicoaluminophosphates.

Non-zeolitic molecular sieves include molecular sieves which have the proper effective pore size and are embraced by an empirical chemical composition, on an anhydrous basis, expressed by the empirical formula:

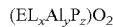

where EL is an element selected from the group consisting of silicon, magnesium, zinc, iron, cobalt, nickel, manganese, chromium, and mixtures thereof, x is the mole fraction of EL and is at least 0.005, y is the mole fraction of Al and is at least 0.01, z is the mole fraction of P and is at least 0.01 and x+y+z=1. When EL is a mixture of elements, x represents the total amount of the metal mixture present. Preferred elements (EL) are silicon, magnesium, and cobalt with silicon being especially preferred. The preparation of various ELAPOs is well known in the art and may be found in U.S. Pat. No. 5,191,141 (ELAPO); U.S. Pat. No. 4,554,143 (FeAPO); U.S. Pat. No. 4,440,871 (SAPO); U.S. Pat. No. 4,853,197 (MAPO, MnAPO, ZnAPO, CoAPO); U.S. Pat. No. 4,793,984 (CAPO); U.S. Pat. No. 4,752,651 and U.S. Pat. No. 4,310,440 all of which are incorporated by reference.

An especially preferred embodiment is one in which EL is silicon (usually referred to as SAPO). The SAPOs which can be used in the instant invention are any of those described in U.S. Pat. No. 4,440,871; U.S. Pat. No. 5,126,308, and U.S. Pat. No. 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 angstroms. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 angstroms and less than about 5.0 angstroms.

The preferred catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength and the like, to the solid particles. Such matrix materials are often to some extent porous in nature and may or may not be effective to promote the desired hydrocarbon conversion. The matrix materials may promote conversion of the feed stream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-beryllias, silica-titanias, silica-alumina-thorias, silica-alumina-zirconias, aluminophosphates, mixtures of these, and the like.

If matrix materials, e.g., binder and/or filler materials, are included in the catalyst composition, the non-zeolitic and/or zeolitic molecular sieves preferably comprise about 1 to 99 percent, more preferably about 5 to about 90 percent, and still more preferably about 10 to about 80 percent by weight of the total composition. The preparation of solid particles comprising catalyst and matrix materials is conventional and well known in the art and, therefore, need not be discussed in detail herein.

The foregoing disclosure and following examples are presented only to illustrate certain specific embodiments of the invention, and should not be construed to limit the scope of the invention as set forth in the claims. There are many possible other variations within the spirit of the invention, as those of ordinary skill in the art will recognize.

EXAMPLES

Comparative coking tests were performed to demonstrate the effects of the present invention. The feed stream used in the tests was blended to simulate the composition in the dense-phase zone of a fluidized-bed reactor for the conversion of methanol to light olefins, with the following composition in wt-%:

| | |
|---|---|
| $H_2$ | 0.0328 |
| CO | 0.2300 |
| $CO_2$ | 0.0072 |
| $CH_4$ | 3.7100 |
| $C_2H_4$ | 15.6000 |
| $C_2H_6$ | 0.2240 |
| $C_3H_6$ | 15.5600 |
| $C_3H_8$ | 0.2500 |
| $C_4$ | 4.7800 |
| $C_5$ | 0.0023 |
| $C_6$ | 0.3900 |
| $H_2O$ | 57.0500 |
| Methanol | 0.7700 |
| Other | 1.3937 |

Example 1

Two comparative tests were carried out with the above feed stream in ⅞-inch Type-316 stainless steel reactors. One reactor was uncoated and one reactor was coated with a layer of tin paint comprising tin octanoate and having a thickness of 0.5-mils. The above feed stream was directed to each of the reactors at a rate of 157 grams per hour. Operating conditions comprised a temperature of 520° C. at a pressure of 290 kPa and a residence time of 6 seconds. Material was collected from the thermowell of each reactor following a 7-day test, with substantially less material collected from the tin-coated reactor. The material collected from the uncoated reactor was determined by Scanning Electron Microscope (SEM) to be filamentous coke, while no filamentous coke was collected from the tin-coated reactor.

Figure 2A:
FIG. 2 shows the presence of coke in an experimental control reactor in comparison to a reactor of the invention.
Figure 2B:
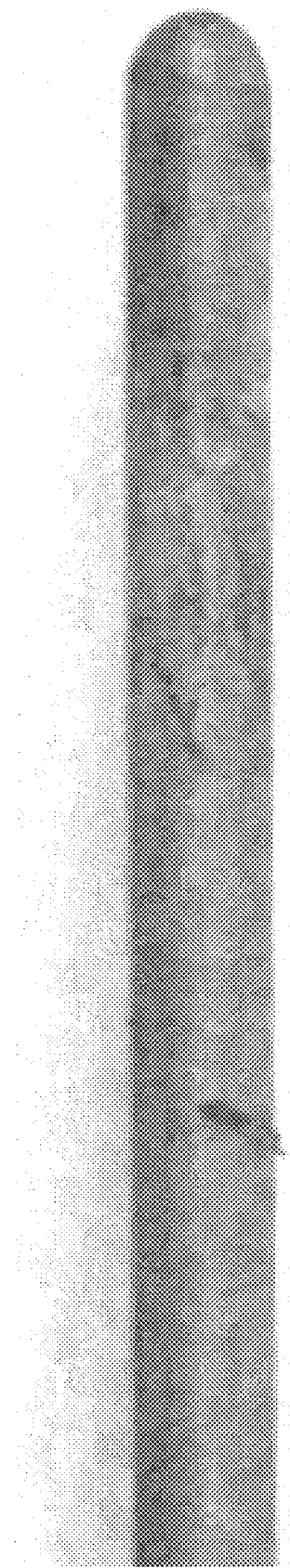

FIG. 2 shows photographs of the thermowells from the two reactors. The 2(a) thermowell is a control from the uncoated reactor, showing the presence of coke. The 2(b) thermowell is from the tin-coated reactor of the invention, showing no substantial evidence of coking.

Example 2

Figure 3A:
FIG. 3 shows the comparative presence of filamentous coke on control coupons in comparison to coupons processed according to the invention.
Figure 3B:
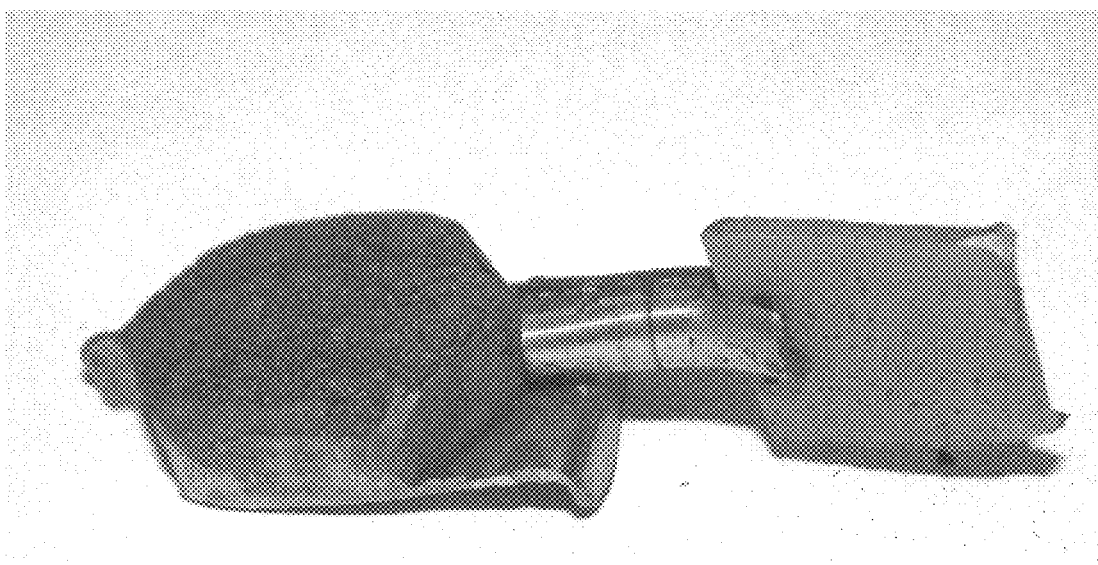

Further tests were carried out with the above feed respectively in uncoated and coated reactors as in Example 1, with results as shown in FIG. 3. Two ¹⁄₁₆-inch-thick coupons were placed in each reactor, one each of a alloysteel square and one of a Hexmesh refractory hexagon, each coupon having dimensions of ¾-inch between parallel sides. The feed stream described above was introduced into each reactor at a rate of 157 grams per hour with operating conditions as in Example 1 of 520° C. at a pressure of 290 kPa and a residence time of 6 seconds. Material was deposited on the coupons in the stainless steel reactor following a 4-day test, as illustrated in test 2(a), which was determined by SEM to be filamentous coke. Following a similar 4-day test in the tin-coated reactor, the coupons remained substantially coke-free as shown in test 2(b). Further investigation of the 2(b) coupons showed that tin had migrated onto the coupons and was associated with the iron, indicating that the tin thereby suppressed coke formation.

Example 3

Two comparative tests were carried out in uncoated and coated reactors as in Example 1. A feed comprising 66 mol-% methanol and 34 mol-% nitrogen was directed to each of the reactors at a residence time of 45 seconds. Operating conditions comprised a temperature of 450° C. at a pressure of 240 kPa. Product gases were analyzed with the following result for the light-gas portion in mol-%:

| | Uncoated | Coated |
|---|---|---|
| $H_2$ | 21.23 | 1.5 |
| $O_2$/A | 0.02 | 0.1 |
| $N_2$ | 55.635 | 82.31 |
| CO | 7.87 | 0.22 |
| $CO_2$ | 1.43 | 0.05 |
| $CH_4$ | 1.1 | 0.92 |
| $C_2H_6$ | 0.02 | 0.01 |

The results indicated that 9.7% of the methanol decomposed in the uncoated reactor in comparison to 0.8% in the tin-coated reactor.

What is claimed is:

1. A process to convert a feed stream comprising an oxygenate in a fluidized-bed reaction zone at conversion conditions in the presence of a catalyst to yield a product stream comprising light olefins, wherein one or more of the internal surfaces of the reaction zone comprises a protective layer resistant to metal-catalyzed coking wherein the protective layer comprises one or more of the group consisting of tin, chromium, antimony, aluminum, germanium and silicon.

2. The process of claim 1 wherein the fluidized-bed reaction zone comprises a fast-fluidized-bed reactor.

3. The process of claim 1 wherein the one or more of the internal surfaces comprises one or both of a steel surface and a refractory lining.

4. The process of claim 1 wherein the protective layer consists essentially of tin.

5. The process of claim 1 wherein the protective layer comprises silicon.

6. The process of claim 1 wherein the catalyst comprises a non-zeolitic silicoaluminophosphate catalyst.

7. The process of claim 1 wherein the oxygenate is selected from the group consisting of methanol, ethanol, propanol, dimethyl ether, and mixtures thereof.

8. A process to convert a feed stream comprising an oxygenate in a fluidized-bed reaction zone at conversion conditions in the presence of a catalyst to yield a product stream comprising light olefins wherein said fluidized-bed reaction zone comprises one or more internal surfaces, further comprising introducing an organometallic compound in the feed stream to reduce metal-catalyzed coking wherein the organometallic compound comprises a compound of one or more of the group consisting of tin, chromium, antimony, aluminum, and germanium.

9. The process of claim 8 wherein the fluidized-bed reaction zone comprises a fast-fluidized-bed reactor.

10. The process of claim 8 wherein the one or more of the internal surfaces comprises one or both of a steel surface and a refractory lining.

11. The process of claim 8 wherein the organometallic compound is introduced on an intermittent basis.

12. The process of claim 8 wherein the organometallic compound consists essentially of a tin compound.

13. The process of claim 8 wherein the catalyst comprises a non-zeolitic silicoaluminophosphate catalyst.

14. The process of claim 8 wherein the oxygenate is selected from the group consisting of methanol, ethanol, propanol, dimethyl ether, and mixtures thereof.

* * * * *